(12) United States Patent
Gu

(10) Patent No.: US 10,959,625 B2
(45) Date of Patent: Mar. 30, 2021

(54) ELECTRONIC APPARATUS AND METHOD CAPABLE OF REDUCING OR AVOIDING OFFSET INTERFERENCE AND ACCURATELY MEASURING PHYSIOLOGICAL CHARACTERISTICS OF USER

(71) Applicant: PixArt Imaging Inc., Hsin-Chu (TW)

(72) Inventor: Ren-Hau Gu, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 635 days.

(21) Appl. No.: 15/785,416

(22) Filed: Oct. 16, 2017

(65) Prior Publication Data

US 2018/0296106 A1 Oct. 18, 2018

(30) Foreign Application Priority Data

Apr. 18, 2017 (TW) ................................ 106112887

(51) Int. Cl.
*A61B 5/024* (2006.01)
*A61B 5/00* (2006.01)

(52) U.S. Cl.
CPC ...... *A61B 5/02427* (2013.01); *A61B 5/02438* (2013.01); *A61B 5/7207* (2013.01); *A61B 5/7257* (2013.01); *A61B 2560/0223* (2013.01)

(58) Field of Classification Search
CPC ............ A61B 5/02427; A61B 5/02438; A61B 5/02416; A61B 5/02433; A61B 5/7207; A61B 5/7257; A61B 2560/0223
See application file for complete search history.

(56) References Cited

U.S. PATENT DOCUMENTS

| 2006/0094943 A1* | 5/2006 | Van Slyke | A61B 5/14551 |
| | | | 600/323 |
| 2006/0293574 A1* | 12/2006 | Norris | A61B 5/7207 |
| | | | 600/323 |
| 2010/0152600 A1* | 6/2010 | Droitcour | A61B 5/1114 |
| | | | 600/534 |
| 2012/0195486 A1* | 8/2012 | Kirenko | A61B 5/02416 |
| | | | 382/131 |
| 2013/0296666 A1* | 11/2013 | Kumar | G01N 21/3151 |
| | | | 600/310 |

FOREIGN PATENT DOCUMENTS

| CN | 1692874 A | 11/2005 |
| CN | 101730503 A | 6/2010 |
| CN | 105249939 A | 1/2016 |
| CN | 105491943 A | 4/2016 |
| CN | 105832289 A | 8/2016 |
| CN | 106456030 A | 2/2017 |

\* cited by examiner

*Primary Examiner* — Devin B Henson
(74) *Attorney, Agent, or Firm* — Winston Hsu

(57) ABSTRACT

A method for measuring physiologically characteristics of user includes: using at least one light emitting unit to emit light ray including first light component corresponding to first wavelength and second light component corresponding to second wavelength different from the first wavelength; using an image sensing circuit to sense and generate at least one physiologically characteristics measurement signal in response to the light ray; performing an offset calibration operation upon the physiologically characteristics measurement signal to generate at least one calibrated measurement signal; and, calculating the calibrated measurement signal to estimate a physiologically characteristics result.

12 Claims, 4 Drawing Sheets

ELECTRONIC APPARATUS AND METHOD CAPABLE OF REDUCING OR AVOIDING OFFSET INTERFERENCE AND ACCURATELY MEASURING PHYSIOLOGICAL CHARACTERISTICS OF USER

BACKGROUND OF THE INVENTION

1. Field of the Invention

The invention relates to a physiologically characteristics measurement mechanism, and more particularly to an electronic apparatus and method for measuring physiologically characteristics.

2. Description of the Prior Art

Generally speaking, a conventional photoplethysmography (PPG) sensing scheme may employ multiple light wavelengths to detect a user's heart rate. However, the performance of conventional scheme is easily impacted by motion artifacts, optical sensing system itself, and/or external noises. The impact of motion artifacts, optical sensing system itself, and/or external noises usually leads to offsets of the estimation of PPG signal. Thus, the result of heart rate detection may be erroneous. Even the conventional scheme may directly adopt PPG signals of two different light wavelengths to calculate a ratio to partially alleviate the impacts. However, the impacts of motion artifacts, optical sensing system itself, and/or external noises have become insurmountable problems for the conventional scheme.

SUMMARY OF THE INVENTION

Therefore one of the objectives of the invention is to provide an electronic apparatus and method for measuring physiologically characteristics, to solve the above-mentioned problems.

According to embodiments of the invention, an electronic apparatus for measuring physiologically characteristics is disclosed. The electronic apparatus comprises at least one light emitting unit, an image sensing circuit, and a processing circuit. The at least one light emitting unit is configured to emit at least one light ray comprising a first light component corresponding to a first wavelength and a second light component corresponding to a second wavelength different from the first wavelength. The image sensing circuit is configured to sense and generate at least one physiologically characteristics measurement signal in response to the at least one light ray. The processing circuit is coupled to the image sensing circuit and configured to perform an offset calibration operation upon the at least one physiologically characteristics measurement signal, generate at least one calibrated physiologically characteristics measurement signal, and calculate the at least one calibrated physiologically characteristics measurement signal to estimate and obtain a physiologically characteristics result.

According to the embodiments, a method for measuring physiologically characteristics is disclosed. The method comprises: utilizing at least one light emitting unit to emit at least one light ray, the at least one light ray comprising a first light component corresponding to a first wavelength and a second light component corresponding to a second wavelength different from the first wavelength; utilizing an image sensing circuit to sense and generate at least one physiologically characteristics measurement signal in response to the at least one light ray; performing an offset calibration operation upon the at least one physiologically characteristics measurement signal to generate at least one calibrated physiologically characteristics measurement signal; and, calculating the at least one calibrated physiologically characteristics measurement signal to estimate and obtain a physiologically characteristics result.

According to the embodiments, the embodiments provide the advantages of solving the above-mentioned problems, providing the capability of anti-motion-artifacts for PPG sensors, and increasing the accuracy of heart rate detection. The embodiments are to improve the heart rate detection affected by motion artifacts by calibrating or correcting offsets of PPG signals of multiple light wavelengths. For example, the embodiments are to obtain PPG signals of two different light wavelengths, respectively remove direct-current offsets caused by motion noises, and calculating a ratio of the PPG signals after removing direct-current offsets or performing motion noise removing, to effectively improve the performance degraded due to the impact of motion artifacts.

These and other objectives of the present invention will no doubt become obvious to those of ordinary skill in the art after reading the following detailed description of the preferred embodiment that is illustrated in the various figures and drawings.

DETAILED DESCRIPTION

The embodiments of the invention are used to decrease or avoid the offsets of photoplethysmogram (PPG) signals caused by motion artifacts, optical sensing system itself and/or external noises. The motion artifacts usually result from inaccurate sensing of physiologically characteristics due to motion of a user. For example, a user wears a wrist-type electronic apparatus on his/her wrist wherein the apparatus is capable of detecting physiologically characteristics. Inevitably, the user's slight finger typing action will significantly affect the performance of wrist-type electronic apparatus and thus lead to inaccuracy of physiologically characteristics sensing. Additionally, the offsets caused by the optical sensing system itself usually result from a slight manufacturing difference of each optical sensing device and also leads to inaccuracy of physiologically characteristics sensing. Additionally, the offsets caused by external noises may result from the external nose sensed by a sensor when the light ray is incident to the sensor. The sensed external noises also lead to inaccuracy of physiologically characteristics sensing. In the embodiments, an electronic apparatus and corresponding method are provided to decrease or avoid the offsets of PPG signals caused by motion artifacts, optical sensing system itself and/or external noises, and more particularly to decrease or avoid direct-current offsets which may affect the estimation of PPG signals. Through estimating and calibrating/correcting offset of at least one PPG signal, the estimation of physiologically characteristics such as the heart rate can be performed based on the corrected PPG signals to obtain more accurate sensing results for physiologically characteristics without being affected by motion artifacts, optical sensing system itself, and external noises. The embodiments are described in the following.

Figure 1:
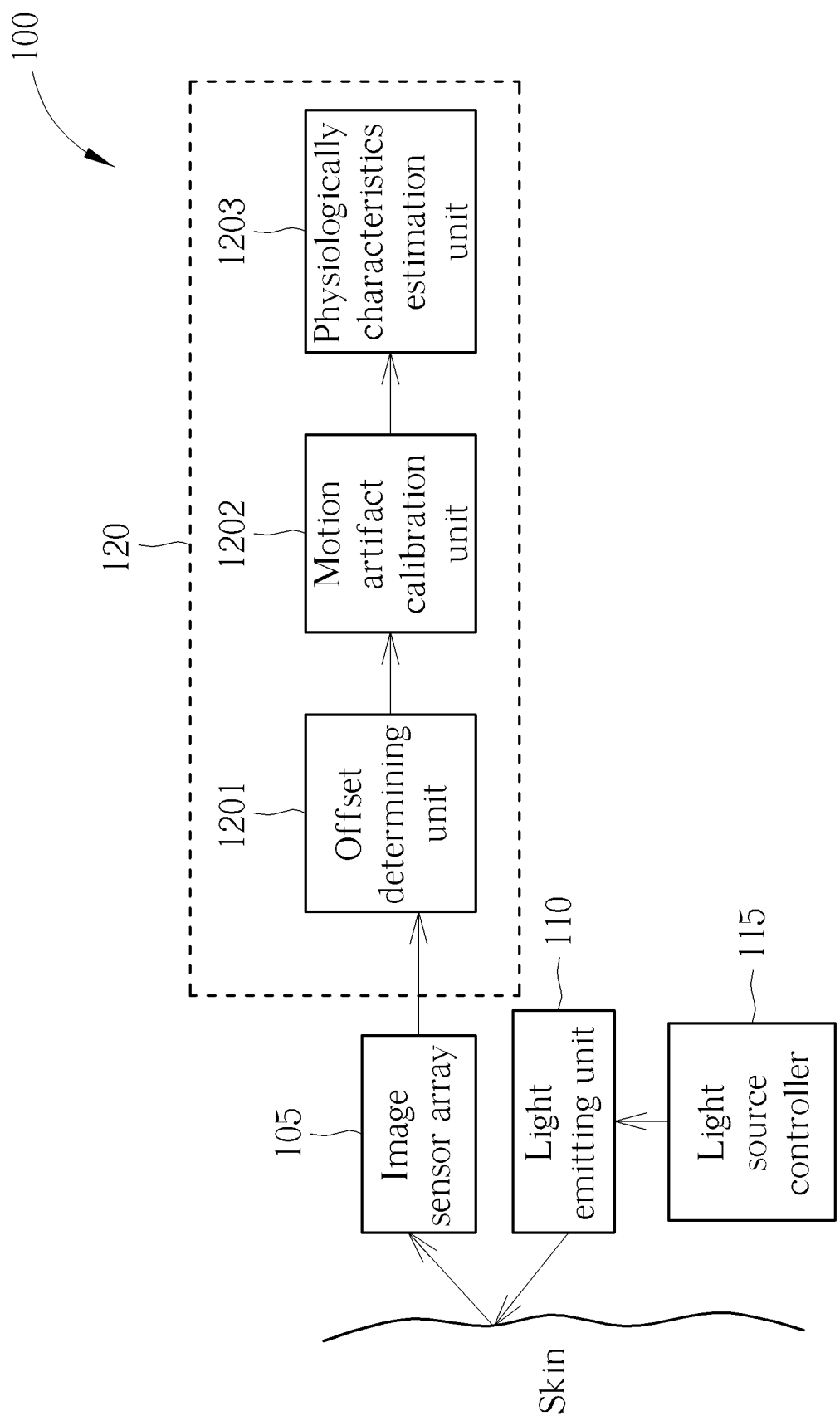
FIG. 1 is a block diagram of an electronic apparatus for measuring physiologically characteristics of users according to an embodiment of the invention.

Please refer to FIG. 1, which is a block diagram of an electronic apparatus 100 for measuring physiologically characteristics of users according to an embodiment of the invention. The electronic apparatus 100 comprises an image sensing circuit 105 (e.g. an image sensor array), at least one light emitting unit 110, a light source controller 115, and a processing circuit 120. In practice, the electronic apparatus 100 can be a portable electronic apparatus or a wearable device such as a smart watch device or a wristband device. The processing circuit 120 comprise an offset determining unit 1201, a motion artifact calibration unit 1202, and a physiologically characteristics estimation unit 1203.

The light source controller 115 such as a light emitting diode (LED) controller can be used for controlling the at least one light emitting unit 110. The at least one light emitting unit 110 is for example an LED and is used for emitting at least one light ray to skin surfaces of a user corresponding to the electronic apparatus 100, to make red blood cells of user blood absorb the emitted light rays in response to different absorption rates of different light rays and thus reflect images on the image sensing circuit 105 to obtain photoplethysmography (PPG) signals of different light rays to thereby estimate the user's physiologically characteristics result such as the user's heart rate. In practice, the at least one light emitting unit 110 for example comprises a white light LED or comprises multiple LEDs (such as red light LED and green light LED, but not limited thereto) corresponding to different wavelengths of different light rays. The light ray emitted by the white light LED includes light components of multiple different light wave lengths. The multiple LEDs are used for respectively emit light components corresponding to different light wavelengths independently at different timings to user's skin surface. It should be noted that the at least one light emitting unit 110 can be implemented by a variety of different circuits and these implementations all fall within the scope of the invention.

The image sensing circuit 105 is arranged for sensing light components having different wavelengths to generate different PPG signals. In practice, if the light emitting unit 110 is implemented by using white light LED (s), the image sensing circuit 105 is arranged to employ a color filter array (CFA) 1051 having multiple color channels corresponding to different wavelengths of light rays to respectively filter and obtain light components having different wavelengths of light rays such as light components of red light wave length, green light wave length, and blue light wave length. The image sensing circuit 105 then is arranged for respectively imaging to generate different PPG signals according to the light components of red light wave length, green light wave length, and blue light wave length. Additionally, if light emitting unit 110 is implemented by using multiple different LEDs corresponding to different wavelengths of light rays such as a first wavelength of red light and a second wavelength of green light, it is not required for the image sensing circuit 105 to employ the color filter array; the image sensing circuit 105 can be arranged to generate a PPG signal of red light wavelength according to the signal imaged due to absorption of user's blood for the light ray emitted by red LED at a first timing and generate a PPG signal of green light wavelength according to the signal imaged due to absorption of user's blood for the light ray emitted by green LED at a second timing, respectively. Thus, the image sensing circuit 105 can respectively generate different PPG signals according to light components having different wave lengths. Therefore, in response to different designs of light emitting unit 110, the above-mentioned color filter array 1051 is optional. This is not meant to be a limitation.

The measured PPG signals can be used to estimate the physiologically characteristics, i.e. the physiologically characteristics measurement signal(s). It should be noted that each PPG signal mentioned above may be affected by offsets or may be not affected by offsets. Thus, after generating the above-mentioned physiologically characteristics measurement signal(s), in order to reduce or avoid offsets caused by motion artifacts, the optical sensing system itself and/or external noises, the processing circuit 120 is arranged to receive at least one physiologically characteristics measurement signal mentioned above, correct the offset of the at least one physiologically characteristics measurement signal to generate at least one corrected physiologically characteristics measurement signal, and then calculate and estimate a physiologically characteristics result such as the user's heart rate according to the at least one corrected physiologically characteristics measurement signal. The operation of processing circuit 120 is detailed in the following.

Specifically, the processing circuit 120 comprises an offset determining unit 1201, a motion artifact calibration unit 1202, and a physiologically characteristics estimation unit 1203. For a physiologically characteristics measurement signal (i.e. PPG signal), the offset determining unit 1201 is arranged to generate or estimate an offset correcting value of the PPG signal, and the motion artifact calibration unit 1202 is arranged to correct the offset of the PPG signal to generate a corrected PPG signal according to the offset correcting value. Then the physiologically characteristics estimation unit 1203 for example is arranged to estimate the user's heart rate according to the corrected PPG signal. The above operations can be implemented by software elements, hardware circuits, and/or a combination of software elements and hardware circuits. That is, the above-mentioned processing circuit 120 and units 1201 to 1203 can be implemented by employing software elements, hardware circuits, or a combination of software elements and hardware circuits. For software elements, each of the units 1201 to 1203 can be a software unit comprised by a specific program code, and the processing circuit 120 for example is a processor which is used to execute the specific program code to perform the above-mentioned offset calibration operation and physiologically characteristics estimation operation. Alternatively, for hardware circuits, the above-mentioned units can be implemented by employing different circuit elements. The above-described implementations all fall within the scope of the invention.

The operation of offset determining unit 1201 for generating or estimating an offset correcting value of a PPG signal is described as follows. For example, the processing circuit 120 is arranged to receive three PPG signals such as different PPG signals respectively corresponding to RGB channels (i.e. different wavelength channels) of red light, green light, and blue light (different light components). In this embodiment, in order to accurately estimate the direct-current offset value, the processing circuit 120 is arranged to perform the physiologically characteristics estimation operation by employing two PPG signals respectively corresponding to two different wavelength channels, e.g. PPG signals of red light wavelength and green light wavelength or PPG signals of blue light wavelength and green light wavelength. Thus, in this example, it is only required to perform the offset calibration operation upon two PPG signals rather than all PPG signals. This is not meant to be a limitation. In other embodiments, the offset calibration operation can be performed for a single one PPG signal or for all PPG signals.

For correcting the direct-current offset value caused by the process/manufacturing variations or a different gain value of an individual pixel, the processing circuit 120 for example can be arranged to retrieve an all-black image (background image) in a first step; in this situation, a sensed value generated by an individual pixel can be regarded as the direct-current offset value. That is, the processing circuit 120 can control the electronic apparatus 100 equivalently operate under the environment of ambient light occlusion. Then, in a second step, the processing circuit 120 is arranged to measure a PPG signal when electronic apparatus 100 operates under the environment of ambient light occlusion, to estimate the direct-current offset value of such PPG signal under the environment of ambient light occlusion as the offset correcting value used for correcting the direct-current offset thereby calibrate the direct-current offset value caused by the process/manufacturing variations or different gain values of individual pixels.

For calibrating the direct-current offset of motion artifact, the calibration operation is performed when the ambient light is not shaded and motion artifact of a specific frequency is applied. The electronic apparatus 100 for example is placed on the user's skin surface and motion artifact of a specific frequency or related noise is applied. The offset determining unit 1201 is arranged to generate multiple different PPG test resultant signals corresponding to red light wavelength by gradually applying or adjusting multiple different direct-current offset test values into a color channel of red light wavelength, and then derive and estimate a direct-current offset correcting value of the PPG signal of red light wavelength. The motion artifact calibration unit 1202 is arranged to use the direct-current offset correcting value to perform an offset calibration upon the PPG signal of red light wavelength. Similarly, the offset determining unit 1201 can be arranged to generate multiple different PPG test resultant signals corresponding to green light wavelength by gradually applying or adjusting multiple different direct-current offset test values into a color channel of green light wavelength, and then derive and estimate a direct-current offset correcting value of the PPG signal of green light wavelength. The motion artifact calibration unit 1202 is arranged to use the direct-current offset correcting value to perform an offset calibration upon the PPG signal of green light wavelength.

For applying or adjusting different direct-current offset test values, these values can be generated by using a fixed step size or through dynamically adjusting a specific step size. Taking an example of fixed step size, its adjustable range for example can be selected as a range from the half of negative value -R_DC to the half of positive value +R_DC, i.e. -R_DC/2~R_DC/2, wherein R_DC means the preliminary direct-current offset of red light wavelength caused by the optical sensing system itself. The fixed step size can be configured as one-twentieth (1/20) of the adjustable range, i.e. R_DC/20. Similarly, the operations of test adjustment for green light wavelength and blue light wavelength are similar to those mentioned above and not detailed for brevity. It should be noted that the above examples are used for illustrative purposes and are not indented to be limitations of the invention.

In addition, in another embodiment, the offset determining unit 1201 can be arranged to gather the statistics result and analyze spectrums of Fourier transform functions of multiple test resultant signals of one or more color channels. For example, the offset determining unit 1201 can adopt the Fourier transform functions such as Fast-Fourier-transform (FFT) to convert each test resultant signal from time domain into the spectrums in frequency domain. Then, the offset determining unit 1201 is arranged to generate a specific threshold according to a maximum energy value of a spectrum of each test resultant signal and a ratio, and is arranged to derive and estimate a direct-current offset correcting value of a PPG signal of a specific light wavelength from multiple different direct-current offset values corresponding to multiple different test resultant signals according to a number of local extreme values of frequency components exceeding above the specific threshold in each test resultant signal. When a number of local extreme values of a specific test resultant signal is smaller than the specific threshold (e.g. a particular/specific number), the offset determining unit 1201 is arranged to select a direct-current offset value corresponding to the specific test resultant signal as the direct-current offset correcting value. The particular/specific number is used as a threshold for determining whether the number of local extreme values is smaller or greater.

Figure 2:
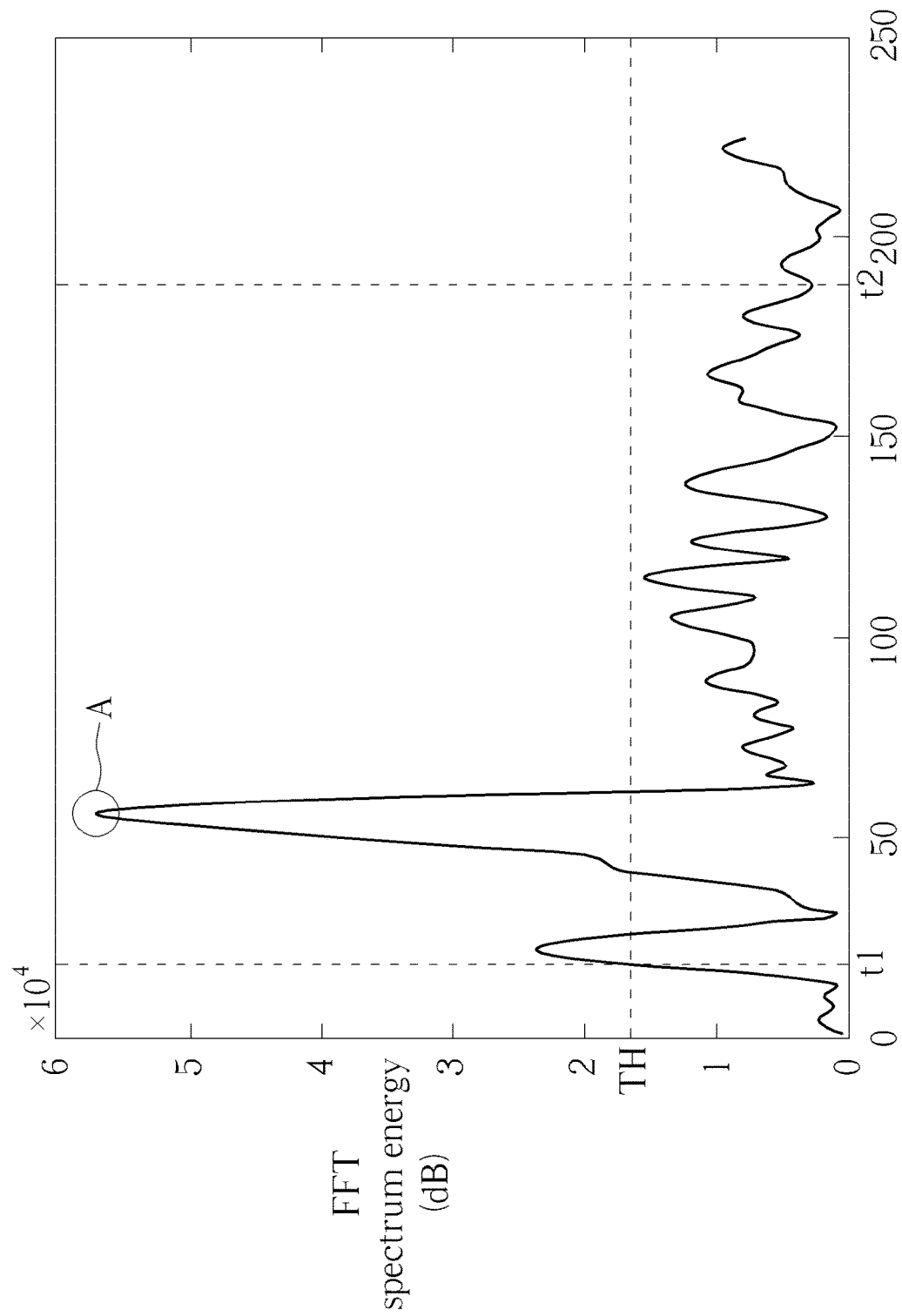
FIG. 2 is a time-frequency analysis diagram showing an example of the FFT spectrum of a test resultant signal when the electronic apparatus of FIG. 1 performs offset calibration/correction.

Refer to FIG. 2, which is a time-frequency analysis diagram showing an example of the FFT spectrum of a test resultant signal when the electronic apparatus of FIG. 1 performs offset calibration/correction. As shown in FIG. 2, X-axis means time while Y-axis means the value of energy intensity of FFT spectrum which indicates signal energy intensity at a particular frequency, and the horizontal dotted line means the specific threshold indicated by TH. In this example, the offset determining unit 1201 detects that the maximum energy value of the spectrum of the test resultant signal is at point A, and then is arranged to adopt the energy value of point A and a ratio such as one-quarter (¼) to calculate and obtain the specific threshold TH. That is, the value of specific threshold TH is equal to one-quarter of the energy value of point A. The offset determining unit 1201 then compares to detect the number of local extreme values of frequency components exceeding above the specific threshold TH in such test resultant signal; in this example, the offset determining unit 1201 detects that the number of local extreme values is equal to two. If the specific threshold (i.e. a specific number) is configured as four, the offset determining unit 1201 can determine/know that the number of local extreme values is equal to two which is smaller than the specific threshold (i.e. four). Thus, in this example, the offset determining unit 1201 is arranged to select the direct-current offset value corresponding to such test resultant signal as the direct-current offset correcting value.

Figure 3:
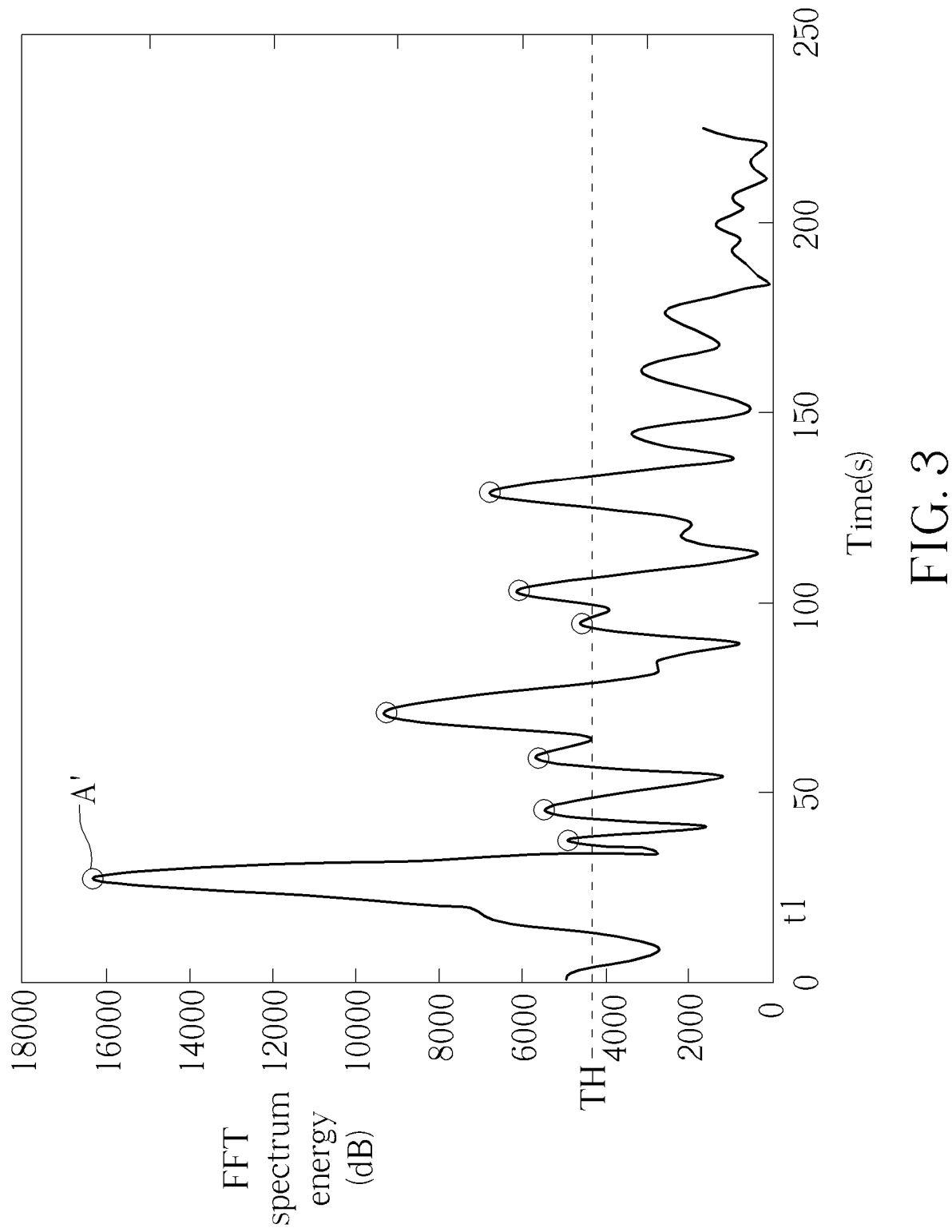
FIG. 3 is a time-frequency analysis diagram showing an example of the FFT spectrum of another test resultant signal when the electronic apparatus of FIG. 1 performs offset calibration/correction.

Refer to FIG. 3, which is a time-frequency analysis diagram showing an example of the FFT spectrum of another test resultant signal when the electronic apparatus of FIG. 1 performs offset calibration/correction. As shown in FIG. 3, X-axis means time while Y-axis means the value of energy intensity of FFT spectrum which indicates signal energy intensity at a particular frequency, and the horizontal dotted line means the specific threshold TH. In this example, the offset determining unit 1201 detects that the maximum energy value of the spectrum of the test resultant signal is at point A', and then is arranged to adopt the energy value of point A' and a ratio such as one-quarter (¼) to calculate and obtain the specific threshold TH. That is, the value of specific threshold TH is equal to one-quarter of the energy value of point A'. The offset determining unit 1201 then compares to detect the number of local extreme values of frequency components exceeding above the specific threshold TH in such test resultant signal; in this example, the offset determining unit 1201 detects that the number of local extreme values is equal to eight. If the specific threshold/number is configured as four, the offset determining unit 1201 can determine/know that the number of local extreme values is equal to eight which is greater than the specific threshold/number (i.e. four). Thus, in this example, the offset determining unit 1201 does not select the direct-current offset value corresponding to such test resultant signal as the direct-current offset correcting value.

When a test resultant signal is converted from time domain into frequency domain, the frequency corresponding to the maximum energy value of the spectrum of the test resultant signal usually indicates the estimated physiologically characteristics, i.e. the heart rate. Ideally, if no direct-current offsets are introduced, the maximum energy value is several times greater than energy values of other frequency components. Accordingly, the ratio such as one-quarter (but not limited) is employed to distinguish the frequency of the maximum energy value from other frequency components. In addition, the above-mentioned specific threshold/number is employed to decide whether the currently used test resultant signal is affected by more or fewer direct-current offsets. For example, as shown in FIG. 2, the number of local extreme values of frequency components exceeding above the specific threshold TH in the test resultant signal is equal to two, and the offset determining unit 1201 decides that the currently used test resultant signal is affected by fewer direct-current offsets. If no other test resultant signals are better than this test resultant signal, the offset determining unit 1201 is arranged to select the direct-current offset value of this test resultant signal as the direct-current offset correcting value. Instead, as shown by FIG. 3, the number of local extreme values of frequency components exceeding above the specific threshold TH in the test resultant signal is equal to eight which is greater than four, and the offset determining unit 1201 decides that the currently used test resultant signal is affected by more direct-current offsets. The offset determining unit 1201 decides not to select the direct-current offset value of this test resultant signal as the direct-current offset correcting value. Based on the above, the offset determining unit 1201 can be arranged to decide and detect qualities of different test resultant signals so as to determine the direct-current offset correcting value.

It should be noted that the offset determining unit 1201 can be arranged to gather and analyze the statistics result based on the energy intensity values within a normal heart rate range such as the range from t1 to t2 as shown in FIG. 2 when performing time-frequency analysis. This is not intended to be a limitation.

When the offset determining unit 1201 finally determines the direct-current offset correcting value, the motion artifact calibration unit 1202 is arranged to calibrate to decrease or reduce the direct-current offset of the PPG signal corresponding to a particular light wavelength. The physiologically characteristics estimation unit 1203 is arranged to estimate the user's heart rate according to corrected PPG signals of two different light wavelengths. In practice, the physiologically characteristics estimation unit 1203 can perform color space conversion upon the PPG signals of two different light wavelengths respectively. Then the physiologically characteristics estimation unit 1203 retrieves the chrominance signals/values of the two PPG signals, calculates a ratio of the chrominance signals/values, and then convert the ratio into frequency domain to determine the heart rate. For example, in one embodiment, if the offset determining unit 1201 respectively determines two offset correcting values of physiologically characteristics measurement signals of color channels of red light wavelength and green light wavelength, the motion artifact calibration unit 1202 is arranged to adopt the two offset correcting values of red light wavelength and green light wavelength to decrease or reduce the direct-current offsets of PPG signals of red light wavelength and green light wavelength. The physiologically characteristics estimation unit 1203 is arranged to respectively perform color space conversion upon the two PPG signals of red light wavelength and green light wavelength, retrieve corresponding chrominance signals of the two PPG signals, calculate the ratio of corresponding chrominance signals, and then convert the ratio into frequency domain to decide the heart rate. The above-mentioned operations are also suitable for processing PPG signals of a set of blue light wavelength and green light wavelength.

Figure 4:
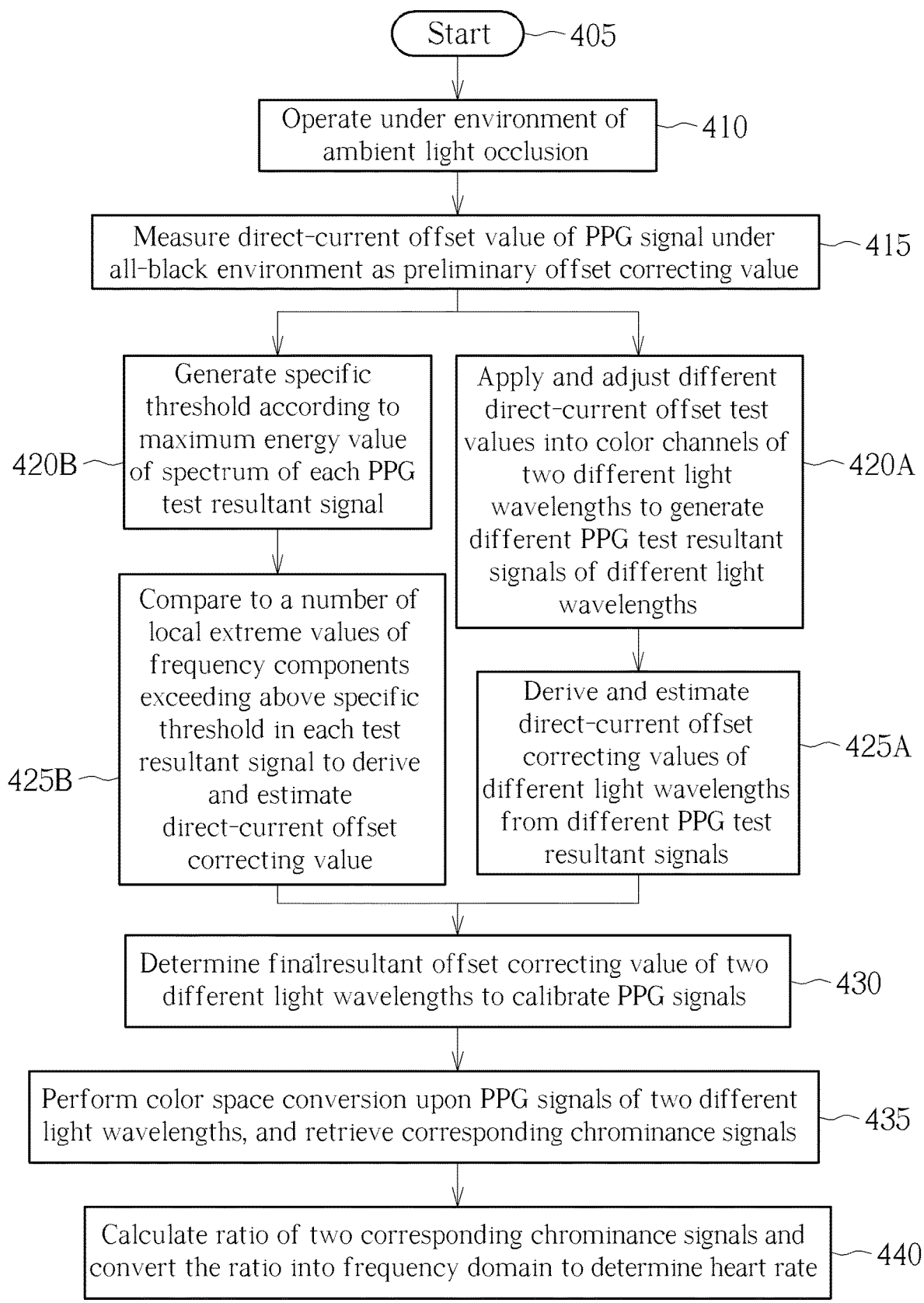
FIG. 4 is a flowchart diagram illustrating the operations of processing circuit as shown in FIG. 1.

To make readers more clearly understand the above operations, the operations of processing circuit 120 in electronic apparatus 100 are described in the steps of flowchart shown in FIG. 4. Provided that substantially the same result is achieved, the steps of the flowchart shown in FIG. 4 need not be in the exact order shown and need not be contiguous, that is, other steps can be intermediate. Steps are detailed in the following:

Step 405: Start;

Step 410: Electronic apparatus 100 operate under the environment of ambient light occlusion (which means almost no ambient light change will applied to the electronic apparatus 100);

Step 415: Measure a direct-current offset value of a PPG signal under the all-black environment and select the measured value as a preliminary offset correcting value;

Step 420A: Respectively apply and adjust multiple different direct-current offset test values into color channels corresponding to two different light wavelengths to generate multiple different PPG test resultant signals corresponding to the different light wavelengths;

Step 425A: Derive and estimate direct-current offset correcting values of different light wavelengths from the multiple different PPG test resultant signals;

Step 420B: Generate a specific threshold according to a maximum energy value of a spectrum of each PPG test resultant signal;

Step 425B: Compare to a number of local extreme values of frequency components exceeding above the specific threshold in each test resultant signal to derive and estimate a direct-current offset correcting value;

Step 430: Determine the final/resultant offset correcting value of two different light wavelengths to calibrate PPG signals of two different light wavelengths;

Step 435: Respectively perform color space conversion upon PPG signals of two different light wavelengths, and retrieve corresponding chrominance signals of two PPG signals; and Step 440: Calculate a ratio of two corresponding chrominance signals and convert the ratio into frequency domain to determine the user's heart rate.

Further, each of the above PPG signals may comprise a value matrix. When calculating offset correcting values, the processing circuit 120 can be arranged to accumulate sensed values of individual pixels by pixels (i.e. pixel-based), accumulate sensed values of pixels at individual columns by columns (i.e. column-based), or accumulate sensed values of pixels of individual frames by frames (i.e. frame-based). All the modifications obey the spirit of the invention.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An electronic apparatus for measuring physiologically characteristics, comprising:
   at least one light emitting unit, configured to emit at least one light ray comprising a first light component corresponding to a first wavelength and a second light component corresponding to a second wavelength different from the first wavelength;
   an image sensing circuit, configured to sense and generate at least one physiologically characteristics measurement signal in response to the at least one light ray; and
   a processing circuit, coupled to the image sensing circuit, configured to perform an offset calibration operation upon the at least one physiologically characteristics measurement signal, to generate at least one calibrated physiologically characteristics measurement signal, and to calculate the at least one calibrated physiologically characteristics measurement signal to estimate and obtain a physiologically characteristics result;
   wherein the processing circuit is arranged to measure a direct-current offset value as a preliminary direct-current offset correcting value utilized by the offset calibration operation when ambient light occlusion; and, the processing circuit is arranged to generate multiple different test resultant signals by gradually applying multiple different direct-current offset test values into at least one color channel corresponding to the at least one light component, derive and estimate the direct-current offset correcting value from the multiple different test resultant signals, and use the direct-current offset correcting value to perform the offset calibration operation upon the at least one physiologically characteristics measurement signal.

2. The electronic apparatus of claim 1, wherein the at least one physiologically characteristics measurement signal comprises a first physiologically characteristics measurement signal corresponding to the first light component and a second physiologically characteristics measurement signal corresponding to the second light component, and the processing circuit comprises:
   a determining unit, configured to estimate a first direct-current offset correcting value corresponding to the first light component and a second direct-current offset correcting value corresponding to the second light component;
   a calibration unit, configured to respectively perform a direct-current offset calibration operation upon the first physiologically characteristics measurement signal and the second physiologically characteristics measurement signal according to the first direct-current offset correcting value and the second direct-current offset correcting value to generate a corrected first physiologically characteristics measurement signal and a corrected second physiologically characteristics measurement signal; and
   an estimation unit, configured to calculate and estimate the physiologically characteristics result according to the corrected first physiologically characteristics measurement signal and the corrected second physiologically characteristics measurement signal.

3. The electronic apparatus of claim 2, wherein the estimation unit is arranged to perform a color space conversion to respectively convert the corrected first physiologically characteristics measurement signal and the corrected second physiologically characteristics measurement signal into a first chrominance signal and a second chrominance signal, to calculate a ratio of the first chrominance signal to the second chrominance signal, and to convert the ratio into a frequency domain to calculate the physiologically characteristics result.

4. The electronic apparatus of claim 1, wherein the processing circuit is arranged to gradually apply the multiple different direct-current offset test values into the color channel by using a fixed step size to generate the multiple different direct-current offset test values or by dynamically adjusting another step size to generate the multiple different direct-current offset test values.

5. The electronic apparatus of claim 1, wherein the processing circuit is arranged to generate a specific threshold according to a maximum energy value of a spectrum of each test resultant signal and a ratio, and derive and estimate the direct-current offset correcting value from the multiple different direct-current offset values corresponding to the multiple different test resultant signals according to a number of local extreme values of frequency components exceeding above the specific threshold in each test resultant signal; and, when a number of local extreme values of a specific test resultant signal is smaller than a specific number, the processing circuit is arranged to select a direct-current offset value corresponding to the specific test resultant signal as the direct-current offset correcting value.

6. The electronic apparatus of claim 1, wherein the at least one physiologically characteristics measurement signal comprises a value matrix, and the processing circuit is able to calculate values of the value matrix by pixels, by columns, or by frames, to calculate an offset correcting value used by a direct-current offset calibration operation.

7. A method for measuring physiologically characteristics, comprising:
   utilizing at least one light emitting unit to emit at least one light ray, the at least one light ray comprising a first light component corresponding to a first wavelength and a second light component corresponding to a second wavelength different from the first wavelength;
   utilizing an image sensing circuit to sense and generate at least one physiologically characteristics measurement signal in response to the at least one light ray;
   performing an offset calibration operation upon the at least one physiologically characteristics measurement signal to generate at least one calibrated physiologically characteristics measurement signal;
   calculating the at least one calibrated physiologically characteristics measurement signal to estimate and obtain a physiologically characteristics result; and
   measuring a direct-current offset value as a preliminary direct-current offset correcting value utilized by the offset calibration operation when ambient light occlusion;
   wherein the step of estimating the at least one direct-current offset correcting value of the at least one light ray further comprises:
   generating multiple different test resultant signals by gradually applying multiple different direct-current offset test values into at least one color channel corresponding to the at least one light component; and deriving and estimating the direct-current offset correcting value from the multiple different test resultant signals.

8. The method of claim 7, wherein the at least one physiologically characteristics measurement signal comprises a first physiologically characteristics measurement signal corresponding to the first light component and a second physiologically characteristics measurement signal corresponding to the second light component, and the method further comprises:

estimating a first direct-current offset correcting value corresponding to the first light component and a second direct-current offset correcting value corresponding to the second light component;

respectively performing a direct-current offset calibration operation upon the first physiologically characteristics measurement signal and the second physiologically characteristics measurement signal according to the first direct-current offset correcting value and the second direct-current offset correcting value to generate a corrected first physiologically characteristics measurement signal and a corrected second physiologically characteristics measurement signal; and calculating and estimating the physiologically characteristics result according to the corrected first physiologically characteristics measurement signal and the corrected second physiologically characteristics measurement signal.

9. The method of claim 8 wherein the step of calculating and estimating the physiologically characteristics result comprises:

performing a color space conversion to respectively convert the corrected first physiologically characteristics measurement signal and the corrected second physiologically characteristics measurement signal into a first chrominance signal and a second chrominance signal;

calculating a ratio of the first chrominance signal to the second chrominance signal; and converting the ratio into a frequency domain to calculate the physiologically characteristics result.

10. The method of claim 7, wherein the step of gradually applying the multiple different direct-current offset test values comprises: using a fixed step size to generate the multiple different direct-current offset test values or dynamically adjusting another step size to generate the multiple different direct-current offset test values.

11. The method of claim 7, wherein the step of deriving and estimating the direct-current offset correcting value from the multiple different test resultant signals comprises:

generating a specific threshold according to a maximum energy value of a spectrum of each test resultant signal and a ratio; and deriving and estimating the direct-current offset correcting value from the multiple different direct-current offset values corresponding to the multiple different test resultant signals according to a number of local extreme values of frequency components exceeding above the specific threshold in each test resultant signal;

wherein when a number of local extreme values of a specific test resultant signal is smaller than a specific number, a direct-current offset value corresponding to the specific test resultant signal is selected as the direct-current offset correcting value.

12. The method of claim 7, wherein the at least one physiologically characteristics measurement signal comprises a value matrix, and an offset correcting value used by a direct-current offset calibration operation is calculated by calculating values of the value matrix by pixels, by columns, or by frames.

* * * * *